United States Patent [19]

Little

[11] Patent Number: 4,821,354

[45] Date of Patent: Apr. 18, 1989

[54] PORTABLE COOLING POOL, BEACH OR CAR SEAT MAT

[76] Inventor: Donald E. Little, 520 Iona St., Metairie, Calif.

[21] Appl. No.: 171,111

[22] Filed: Mar. 21, 1988

[51] Int. Cl.$^4$ .................. A47C 21/04; A47C 27/08
[52] U.S. Cl. .................................. 5/422; 5/449; 5/450; 5/455; 62/259.3; 138/103; 138/108; 138/172; 128/372; 128/400; 105/46
[58] Field of Search .............. 5/451, 450, 449, 455, 5/456, 421, 422; 128/400, 372; 138/103, 108, 172; 62/259.3; 165/46

[56] References Cited

U.S. PATENT DOCUMENTS

| 254,265 | 2/1882 | Bonz | 5/451 |
|---|---|---|---|
| 500,568 | 7/1893 | Ells | 5/421 |
| 1,928,942 | 10/1933 | Clark et al. | 138/103 |
| 2,930,594 | 3/1960 | Macracken | 128/400 |
| 4,010,795 | 3/1977 | Stenberg | 128/400 |
| 4,114,620 | 9/1978 | Moore et al. | 5/455 |
| 4,420,016 | 12/1983 | Nichols | 138/103 |

Primary Examiner—Alexander Grosz
Attorney, Agent, or Firm—Freilich, Hornbaker, Rosen & Fernandez

[57] ABSTRACT

A mat for cooling a person on the beach, side of a swimming pool, and even in a vehicle, is provided with recirculated ice water from an insulated reservoir using a small battery powered pump. The mat is made of sheets of urethane coated nylon or PVC film that is heat sealed on all sides, and to tubes that contain the ice water in and out. The sheets are also sealed to provide channels that hold extruded strips so formed as to assure that ice water will continue to flow through the channels even when the weight of the person would tend to close the space between the sheets.

3 Claims, 3 Drawing Sheets

PORTABLE COOLING POOL, BEACH OR CAR SEAT MAT

BACKGROUND OF THE INVENTION

This invention relates to a self-contained, portable water recirculating cooling mat for use at a swimming pool, beach or vehicle seat using ice water driven by a motor powered by a rechargeable battery.

There is often a strong need of a cooling mat which can cool for a long time, typically as long as 4 hours, at high temperatures (80° F.) while sun bathing at the beach or side of a swimming pool. There is a similar need for cooling the seat of an automobile, truck, tractor or other vehicle.

A search for a cooling mat led to a cooling vest that is worn over the chest and uses a recirculating air system. However, no system for cooling a mat in the present form of a vest can achieve the desired degree of cooling by using recirculating ice water because of body weight restriction on the recirculation of the ice water.

SUMMARY OF THE INVENTION

This problem of adapting a cooling vest to a water cooled mat has been overcome by inserting extruded strips in channels formed within the mat. The cross section of the strips has grooves which prohibit the two outer sides of the mat from being compressed by a persons body weight, thus allowing a flow of ice water from a portable reservoir to continually flow under the person lying on the mat.

In accordance with the present invention, a long mat of urethane coated nylon or PVC film is sealed together to form a bladder with channels running from near one end to the other, and with a common section at each end in communication with each channel. An extruded resilient plastic or rubber strip having grooves along the entire length is inserted in every channel to assure that the body weight will not collapse the channels and prevent cooling water to pass through from one common section to another at the other end. Thus, the strips effectively allow water to pass through the channels even while the weight of a person is on the mat. The water is recirculated through the mat bladder from a portable reservoir of ice water by a small pump powered by a rechargeable battery (not shown).

A second embodiment comprises a foam mat below the cooling bladder for insulation from below, and an air bladder with channels for insulation from above, except in those areas where the body weight collapses the air channels.

DESCRIPTION OF PREFERRED EMBODIMENTS

Figure 1:
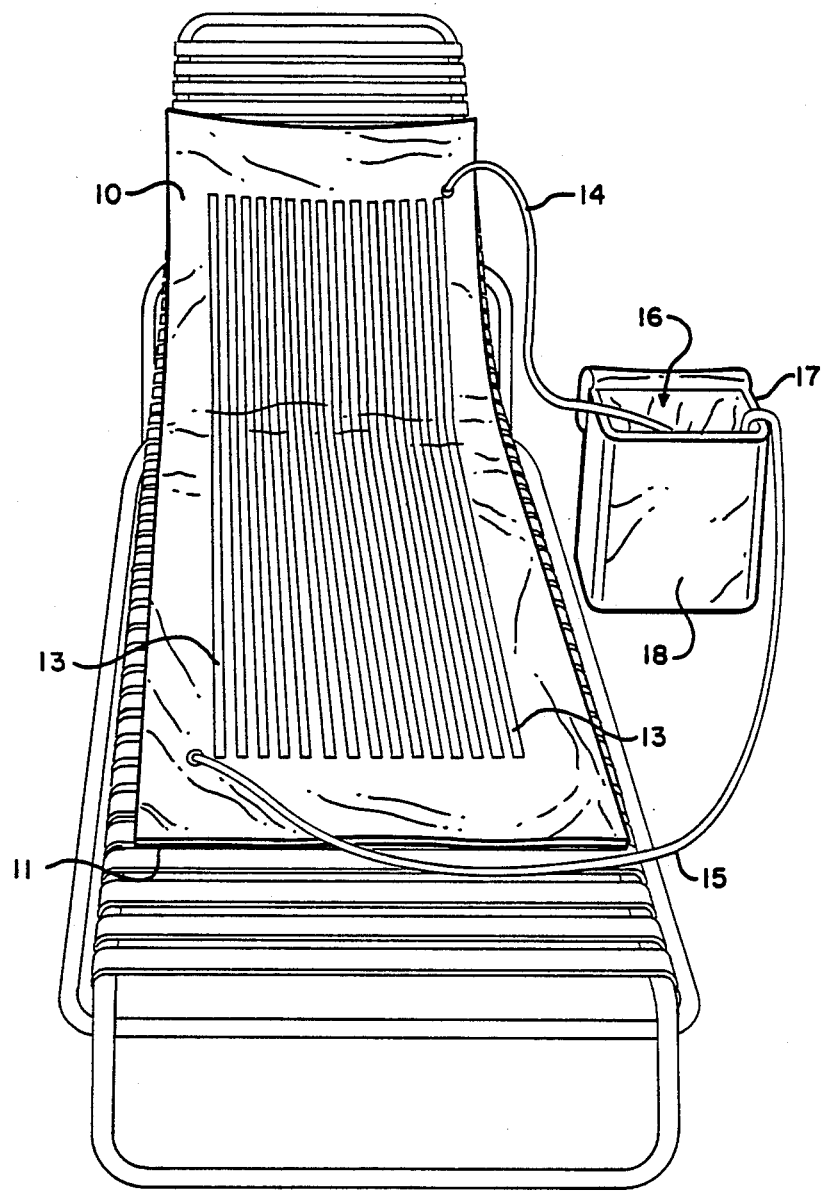
FIG. 1 illustrates a mat that is the subject of this invention on a chaise lounge of a type typically used at a swimming pool for sun bathing.

Referring to FIG. 1, a cooling mat CM is shown on a chaise lounge comprised of two sheets 10 and 11 of polyurethane coated nylon or PVC film. The two sheets are joined together by high frequency heat sealing along all four sides and corners, and between channels that will hold strips 13.

Figure 3:
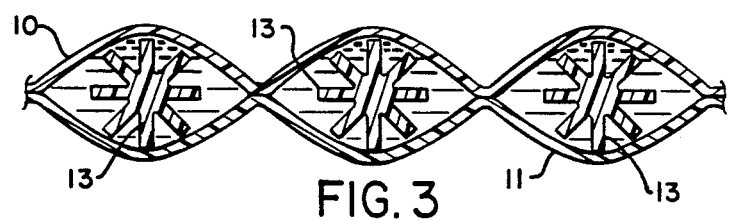
FIG. 3 illustrates in a cross section of three channels in FIG. 1 the manner in which two sheets forming the surface of the mat are heat sealed together to form channels for extruded plastic or rubber strips.
Figure 4:
FIG. 4 illustrates a cross section of a preferred strip to be inserted in the channels.
Figure 2:
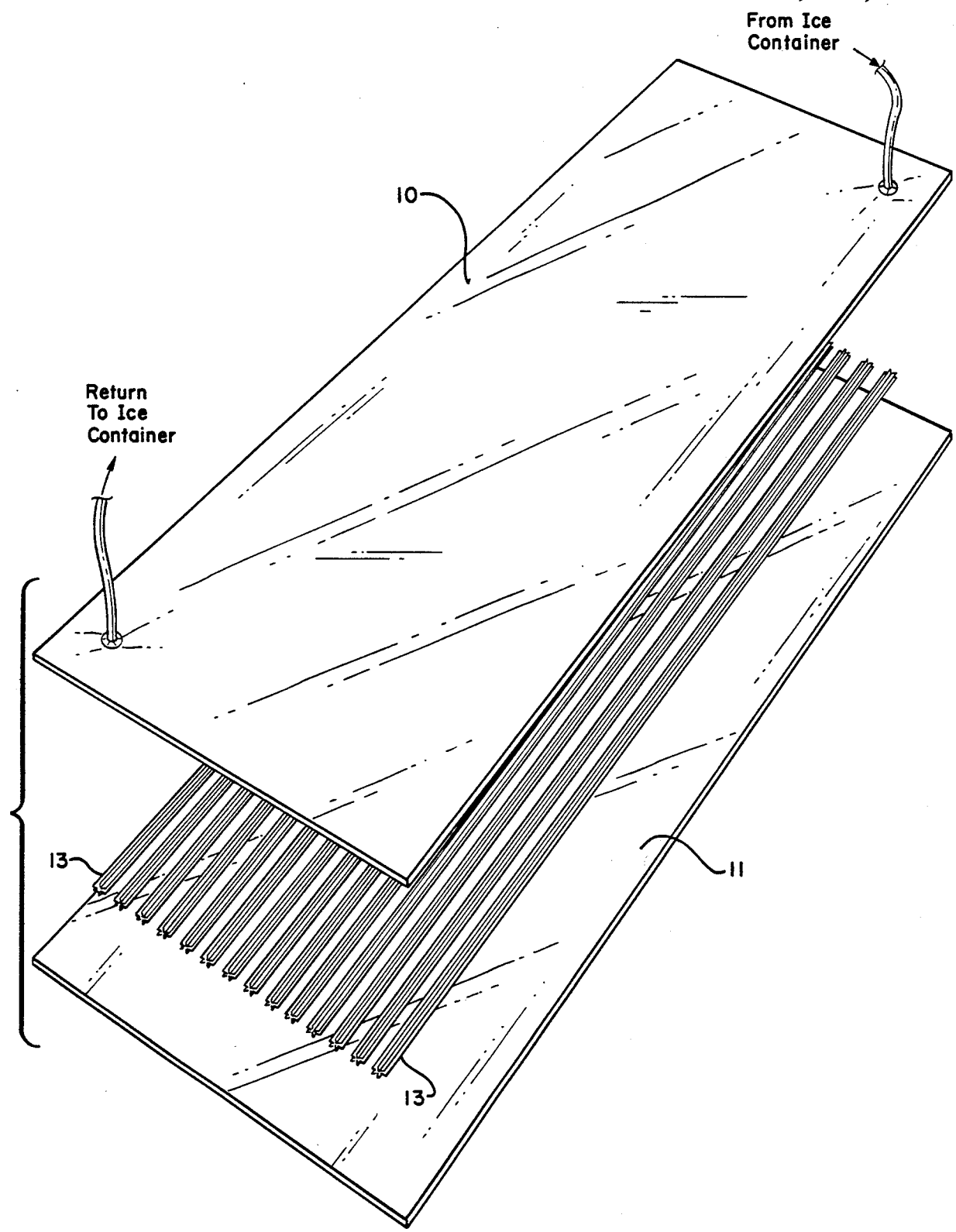
FIG. 2 illustrates in an exploded view the elements of the mat of FIG. 1.

In fabricating the mat, flanges of tubes 14 and 15 are first heat sealed to the sheet 10. Next, the channels between the sheets 10 and 11 are formed by heat sealing. Then plastic or rubber extruded strips are inserted in the channels, and finally the sides, ends and corners are heat sealed. FIG. 3 shows how the strips will maintain passage for cooling water even with the body weight of a person bearing down on the mat. FIG. 4 shows a cross section of an extruded strip that is preferred for insertion in the cooling channels because it well present a more nearly flat surface without causing any reduction in the flow of water through the channels.

The water is forced through the mat by a pump 16 (not shown) in a portable reservoir 17. The reservoir is partially filled with ice and water in the bottom part 18 of the reservoir. The pump is preferably a small battery operated bilge pump of the type that is used in small boats, such as a centrifugal submersible pump model 1P811A manufactured by Teel Water Systems, Dayton Electric Manufacturing Co., Chicago, Ill. 60648.

The reservoir is insulated to keep the recirculating water cool, and is preferably made of urethane coated nylon with a top (shown folded back) made of the same material. This flexible construction for the reservoir facilitates passing the tubes 14 and 15 into the reservoir. The pump injects ice water into the mat through one tube, and allows the excess to continually drain into the reservoir through the other tube.

In practice, either tube can be used for the return of water, particularly when the mat is level on the beach or pool deck, but when it is not level, such as when on a chaise lounge as shown, it is preferred to place it with the return tube to be higher to assure that the mat will fill completely with ice water.

The mat can be used to cover the seat of a vehicle in the same manner as it is used to cover a chaise lounge. It can be placed on the seat across its full length, or it can be placed on the seat and back for just one person, the driver or passenger.

Figure 5:
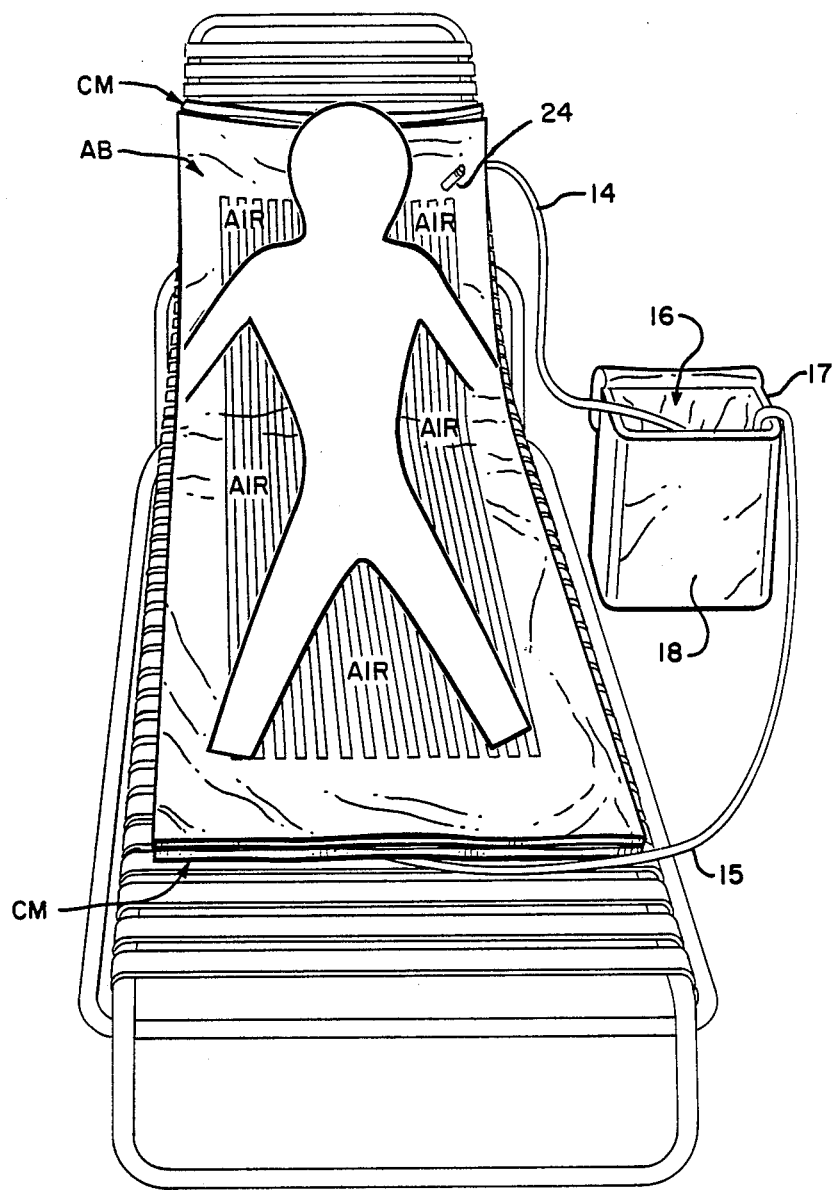
FIG. 5 illustrates a second embodiment of the invention which utilizes a foam mat to insulate the cooling bladder from below, and an air bladder with channels for insulation of the cooling bladder from above, except in those areas where the body weight collapses the air channels.
Figure 6:
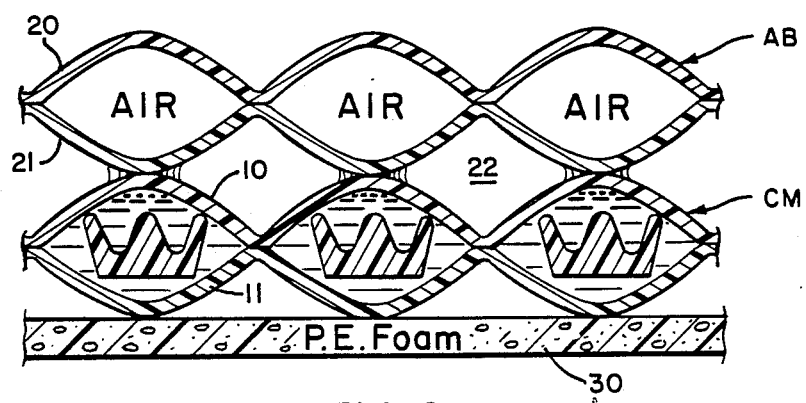
FIG. 6 illustrates in a cross section across three channels in FIG. 5 the manner in which the foam bed, cooling bladder and air bladder are stacked and fused (heat sealed) together where they are in contact while the bladders are inflated with cooling water or air, respectively.

FIG. 5 illustrates an air bladder AB over a cooling unit produced in the same manner as the cooling mat CM of FIG. 1, and heat sealed along the midchannel areas where the air bladder AB contacts the cooling mat CM as shown in FIG. 6. The air bladder is comprised of two sheets 20 and 21 of polyurethane coated nylon or PVC film. To produce the air bladder over the cooling mat, the top sheet 10 of the cooling mat is first heat sealed (fused) to the bottom sheet 21 of the air bladder; then a metal rod is inserted in the resulting channels 22. This rod is used as a backing only while heat sealing the sheets 10 and 20 to the respective sheets 11 and 21 to form the channels for the cooling mat CM and air bladder AB.

Once the channels have been formed, the cooling mat is sealed on all sides as before, and the air bladder is sealed on all sides. While the cooling mat is prepared with separate inlets and outlets on the sheet 10 as before, the air bladder is prepared with simply a single stem 24 on the sheet 20, such as a valve stem shown in FIG. 5, through which air may be pumped using a small bicycle hand pump, and later released to store the cooling mat and air bladder combination.

A foam mat 30 shown in FIG. 6 is cut to the dimensions of the cooling mat CM and air bladder AB is provided for insulation from below. It can be secured to the sheet 11 of the cooling mat where it makes contact along the length of the channels, but in practice it is sufficient to heat seal the sheet 11 to the foam mat 30 only along its edges, or at spaced points along its edges, sufficiently to keep the cooling mat from sliding off the foam mat when in use.

Although particular embodiments of the invention have been described and illustrated herein, it is recognized that modifications and variations may readily occur to those skilled in the art. Consequently, it is intended that the claims be interpreted to cover such modifications and variations.

What is claimed is:

1. A mat for cooling a person lying or sitting on the mat comprising two sheets sealed together to form a cooling bladder, a reservoir containing ice water to be recirculated through said cooling bladder, two tubes connected to said bladder for conveying said ice water from said reservoir and back to said reservoir, one tube being connected at one end of the bladder and the other of said two tubes being connected at the opposite end of said cooling bladder, said two sheets being further sealed together to form parallel channels that are spaced from sealed sides of said cooling bladder and spaced from sealed ends of said cooling bladder thereby to provide flow of said ice water from said one end to said end of said cooling bladder, and extruded strips inserted in said parallel channels to prevent the two sheets from collapsing against each other due to pressure exerted by said person, said strips being extruded with a cross section which will assure a passage of said ice water through said parallel channels even while said person is lying or sitting on said mat, and further including an air bladder connected to one surface of said cooling bladder for insulation of said cooling bladder on said one surface while said person is lying or sitting on said mat.

2. A mat as defined in claim 1 wherein said air bladder is comprised of two separate sheets sealed together for containing air.

3. A mat as defined in claim 2 wherein said two separate sheets are further sealed together to form parallel air channels that are spaced from sealed sides of said air bladder and spaced from sealed ends of said air bladder to provide communication of air between opposite ends of said air bladder.

* * * * *